(12) United States Patent
Acre et al.

(10) Patent No.: US 11,878,619 B2
(45) Date of Patent: Jan. 23, 2024

(54) LIQUID DISPENSING APPARATUS FOR A VEHICLE WITH A DISPENSER AND A SOURCE OF ULTRAVIOLET LIGHT TO SANITIZE THE DISPENSER

(71) Applicant: Ford Global Technologies, LLC, Dearborn, MI (US)

(72) Inventors: James Alan Acre, Monroe, MI (US); Robert D. Bedard, Allen Park, MI (US); John P. Casci, Westland, MI (US); James George Gebbie, Rochester Hills, MI (US); Douglas Raymond Martin, Canton, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 541 days.

(21) Appl. No.: 17/108,611

(22) Filed: Dec. 1, 2020

(65) Prior Publication Data
US 2022/0169165 A1   Jun. 2, 2022

(51) Int. Cl.
*B60N 3/18* (2006.01)
*A61L 2/10* (2006.01)
*C02F 1/32* (2023.01)

(52) U.S. Cl.
CPC .................. *B60N 3/18* (2013.01); *A61L 2/10* (2013.01); *C02F 1/32* (2013.01); *A61L 2202/16* (2013.01)

(58) Field of Classification Search
CPC .................. B60N 3/18; A61L 2/10; C02F 1/32
USPC ........................................... 137/353; 222/190
See application file for complete search history.

(56) References Cited

U.S. PATENT DOCUMENTS

| | | | | | |
|---|---|---|---|---|---|
| 2,669,251 A | * | 2/1954 | Jackson | .................. | B60N 3/18 219/202 |
| 2,813,537 A | * | 11/1957 | Lind | ........................ | B67D 1/04 219/202 |
| 2,830,613 A | * | 4/1958 | Mason | ..................... | B60N 3/18 219/202 |
| 2,915,082 A | * | 12/1959 | Evart | ....................... | B60N 3/18 137/353 |
| 2,975,797 A | * | 3/1961 | Matheney | ................ | B60N 3/18 219/202 |

(Continued)

FOREIGN PATENT DOCUMENTS

| | | |
|---|---|---|
| CN | 102698495 A | 10/2012 |
| CN | 102701474 A | 10/2012 |

(Continued)

*Primary Examiner* — Paul R Durand
*Assistant Examiner* — Michael J. Melaragno
(74) *Attorney, Agent, or Firm* — Vichit Chea; Price Heneveld LLP (57) ABSTRACT

A vehicle comprises: a dispenser for a liquid, the dispenser comprising an outlet for the liquid; and a source of ultraviolet light disposed to emit the ultraviolet light onto the outlet of the dispenser. The dispenser further comprises a first position and a second position that is different than the first position. The outlet of the dispenser is disposed closer to the source of ultraviolet light when the dispenser is in the second position than when the dispenser is in the first position. The vehicle comprises a controller in communication with the source of the ultraviolet light. The controller causes the source of ultraviolet light to emit the ultraviolet light when the dispenser is in the second position but not when the dispenser is in the first position.

20 Claims, 11 Drawing Sheets

(56) References Cited

U.S. PATENT DOCUMENTS

| | | | | |
|---|---|---|---|---|
| 3,276,634 | A * | 10/1966 | Arnot | B60N 3/16 219/202 |
| 3,558,013 | A * | 1/1971 | Ponzo | B60N 3/18 222/394 |
| 3,642,023 | A * | 2/1972 | Rembert | B60N 3/18 222/394 |
| 4,034,571 | A * | 7/1977 | Bollinger | B60N 3/18 62/399 |
| 4,055,279 | A * | 10/1977 | Lapera | B67D 7/80 219/202 |
| 4,130,145 | A * | 12/1978 | Thomas, Jr. | B60N 3/18 280/1 |
| 4,140,150 | A * | 2/1979 | Rundell | B60N 3/18 137/340 |
| 4,342,202 | A * | 8/1982 | Knutson | B60H 1/00592 62/394 |
| 4,566,507 | A * | 1/1986 | Rauchwerger | B60N 3/18 141/271 |
| 5,435,151 | A | 7/1995 | Han | |
| 5,497,918 | A * | 3/1996 | Brilanchik | B67D 1/0004 123/41.31 |
| 5,881,913 | A * | 3/1999 | Boulter | C02F 9/20 222/2 |
| 6,065,939 | A * | 5/2000 | Lin | B60R 15/00 219/202 |
| 6,076,706 | A * | 6/2000 | Kritchman | B60H 1/00285 222/481.5 |
| 6,182,453 | B1 | 2/2001 | Forsberg | |
| 6,481,232 | B2 | 11/2002 | Faqih | |
| 6,684,648 | B2 | 2/2004 | Faqih | |
| 6,755,037 | B2 | 6/2004 | Engel et al. | |
| 6,962,381 | B2 | 11/2005 | Warning | |
| 8,252,174 | B2 | 8/2012 | Jones et al. | |
| 8,322,574 | B1 * | 12/2012 | Phillips | B60N 3/18 219/202 |
| 8,742,364 | B2 | 6/2014 | Boodaghians et al. | |
| 10,513,213 | B1 * | 12/2019 | Mullenaux | B67D 1/0858 |
| 11,292,393 | B1 * | 4/2022 | Baker | B60R 15/00 |
| 2003/0222474 | A1 * | 12/2003 | Liu | B60N 3/102 296/37.8 |
| 2005/0173171 | A1 * | 8/2005 | Daniels | B60N 3/18 180/90 |
| 2005/0188854 | A1 * | 9/2005 | Green | A47J 31/3642 99/275 |
| 2010/0025311 | A1 | 2/2010 | Jones et al. | |
| 2010/0247374 | A1 * | 9/2010 | Pellet | A61L 2/10 422/107 |
| 2011/0232862 | A1 * | 9/2011 | Gofton | B60N 3/16 236/12.12 |
| 2011/0286883 | A1 * | 11/2011 | Hecht | A61L 2/10 250/492.1 |
| 2012/0221198 | A1 | 8/2012 | Kohavi et al. | |
| 2013/0126034 | A1 * | 5/2013 | Sierra | F16L 9/14 138/148 |
| 2014/0042187 | A1 * | 2/2014 | Pesach | B67D 7/80 222/608 |
| 2015/0056096 | A1 * | 2/2015 | Hoover | A61L 9/205 422/24 |
| 2015/0060488 | A1 * | 3/2015 | Rupp | A23G 9/245 222/144.5 |
| 2016/0022849 | A1 * | 1/2016 | Hecht | A61L 2/00 250/455.11 |
| 2016/0029686 | A1 * | 2/2016 | Hecht | A61L 2/00 250/455.11 |
| 2016/0083936 | A1 | 3/2016 | Martin et al. | |
| 2019/0002263 | A1 * | 1/2019 | Chivchyan | B67D 1/0857 |
| 2019/0056751 | A1 | 2/2019 | Ferguson et al. | |
| 2019/0217975 | A1 * | 7/2019 | Casci | B60H 1/32331 |
| 2022/0134931 | A1 * | 5/2022 | Mullenaux | B60N 3/18 137/351 |
| 2022/0135431 | A1 * | 5/2022 | Mullenaux | C02F 1/001 96/409 |
| 2022/0169165 | A1 * | 6/2022 | Acre | A61L 2/24 |
| 2022/0169538 | A1 * | 6/2022 | Acre | C02F 1/32 |
| 2023/0148801 | A1 * | 5/2023 | Sempier | A47K 5/1202 222/608 |

FOREIGN PATENT DOCUMENTS

| | | | |
|---|---|---|---|
| CN | 205044604 U | 2/2016 | |
| CN | 105595836 A | 5/2016 | |
| CN | 105711468 A | 6/2016 | |
| CN | 205523857 U | 8/2016 | |
| CN | 109159643 A | 1/2019 | |
| CN | 110588276 A | 12/2019 | |
| CN | 211308340 U | 8/2020 | |
| CN | 213178911 U | 5/2021 | |
| WO | WO-03009729 A1 * | 2/2003 | ............ A47J 31/005 |
| WO | WO-2004033361 A2 * | 4/2004 | ............ A42B 3/048 |
| WO | WO-2008075346 A2 * | 6/2008 | ............ A47J 31/005 |
| WO | WO-2008098683 A2 * | 8/2008 | ............ A47J 31/005 |
| WO | 2015186143 A2 | 12/2015 | |
| WO | WO-2019197078 A1 * | 10/2019 | ............ A47J 31/005 |

\* cited by examiner

LIQUID DISPENSING APPARATUS FOR A VEHICLE WITH A DISPENSER AND A SOURCE OF ULTRAVIOLET LIGHT TO SANITIZE THE DISPENSER

FIELD OF THE DISCLOSURE

The present disclosure relates to vehicles with a dispenser to dispense liquid, and sanitization of the dispenser with ultraviolet light.

BACKGROUND OF THE DISCLOSURE

A vehicle sometimes includes a dispenser to dispense water. However, there is a general need for the dispenser to dispense the water in a sanitized and potable state.

SUMMARY OF THE DISCLOSURE

The present disclosure addresses that problem by incorporating a source of ultraviolet light into the vehicle to emit the ultraviolet light onto the dispenser to reduce or eliminate the microbes present on the dispenser. The reduction or elimination of the microbes on the dispenser thus limits transfer of microbes to the water that the dispenser dispenses.

According to a first aspect of the present disclosure, a liquid dispensing apparatus for a vehicle comprises: a dispenser comprising an outlet for a liquid; and a source of ultraviolet light disposed to emit the ultraviolet light onto the outlet of the dispenser.

Embodiments of the first aspect of the present disclosure can include any one or a combination of the following features:

- the dispenser further comprises a first position and a second position that is different than the first position;
- the outlet of the dispenser is disposed closer to the source of the ultraviolet light when the dispenser is in the second position than when the dispenser is in the first position;
- in the second position, the outlet of the dispenser is inaccessible from an environment external to the liquid dispensing apparatus;
- the liquid dispensing apparatus further comprises a housing that forms a chamber in which the outlet of the dispenser is disposed when the dispenser is in the second position;
- the source of the ultraviolet light is disposed to emit the ultraviolet light into the chamber;
- the housing comprises a surface forming at least part of the chamber, and the surface reflects the ultraviolet light that the source of the ultraviolet light emits;
- the dispenser further comprises a main body and a conduit extending through the body, the main body comprising an outer surface, and the conduit being in liquid communication with the outlet;
- the housing comprises a movable top wall that (i) extends over the main body of the dispenser, when the dispenser is in the second position, and (ii) forms part of the chamber in which the outlet of the dispenser is disposed when the dispenser is in the second position;
- the source of the ultraviolet light is configured to emit the ultraviolet light onto an entirety of the outer surface of the main body of the dispenser;
- the liquid dispensing apparatus further comprises a sensor configured to output data that changes as a function of whether the dispenser is in the second position; and
- the dispenser is configured to be in liquid communication with a source of liquid that is disposed within the vehicle.

According to a second aspect of the present disclosure, a vehicle comprises: a dispenser for a liquid, the dispenser comprising an outlet for the liquid; and a source of ultraviolet light disposed to emit the ultraviolet light onto the outlet of the dispenser.

Embodiments of the second aspect of the present disclosure can include any one or a combination of the following features:

- the dispenser further comprises a first position and a second position that is different than the first position;
- the outlet of the dispenser is disposed closer to the source of the ultraviolet light when the dispenser is in the second position than when the dispenser is in the first position;
- the vehicle further comprises a controller in communication with the source of the ultraviolet light, the controller causing the source of ultraviolet light to emit the ultraviolet light when the dispenser is in the second position but not when the dispenser is in the first position;
- the vehicle further comprises a sensor in communication with the controller, the sensor configured to output data that changes as a function of whether the dispenser is in the second position;
- the controller causes the source of ultraviolet light to emit the ultraviolet light when the sensor outputs data indicative that the dispenser is in the second position;
- the vehicle further comprises a housing that forms a chamber in which the outlet of the dispenser is disposed when the dispenser is in the second position;
- the source of the ultraviolet light is disposed to emit the ultraviolet light into the chamber;
- the housing comprises a surface forming at least part of the chamber, and the surface reflects the ultraviolet light that the source of the ultraviolet light emits;
- the vehicle further comprises a source of the liquid in liquid communication with the dispenser;
- the vehicle generates the liquid that the dispenser dispenses;
- the vehicle further comprises (i) a center console and (ii) a housing disposed at the center console, the housing comprising a chamber in which the outlet of the dispenser is disposed when the dispenser is in the second position;
- the source of the ultraviolet light is disposed to emit the ultraviolet light into the chamber;
- the dispenser further comprises a main body and a conduit extending through the body, the main body comprising an outer surface, and the conduit being in liquid communication with the outlet;
- the housing comprises a movable top wall that (i) extends over the main body of the dispenser, when the dispenser is in the second position, and (ii) forms part of the chamber in which the outlet of the dispenser is disposed when the dispenser is in the second position; and
- the source of the ultraviolet light is configured to emit the ultraviolet light onto an entirety of the outer surface of the main body of the dispenser;
- the vehicle further comprises an interior configured for an occupant of the vehicle to occupy;
- the dispenser is accessible from the interior; and
- the ultraviolet light that the source of the ultraviolet light emits does not transmit into the interior.

According to a third aspect of the present disclosure, a method of sanitizing a dispenser for a liquid comprises: emitting ultraviolet light onto an outlet of a dispenser for a liquid, wherein, a vehicle comprises the dispenser.

Embodiments of a third aspect of the present disclosure can include any one or a combination of the following features:
- emitting the ultraviolet light occurs as a consequence of the dispenser moving from a first position to a second position;
- the method further comprises ceasing emitting the ultraviolet light onto the outlet of the dispenser; and
- the method further comprises after a preset period of time has passed, again emitting the ultraviolet light onto the outlet of the dispenser;
- the dispenser further comprises a main body and a conduit extending through the body, the main body comprising an outer surface, and the conduit being in liquid communication with the outlet; and
- emitting the ultraviolet light further comprises emitting ultraviolet light onto an entirety of the outer surface of the main body of the dispenser.

These and other aspects, objects, and features of the present disclosure will be understood and appreciated by those skilled in the art upon studying the following specification, claims, and appended drawings.

DETAILED DESCRIPTION OF THE PREFERRED EMBODIMENTS

Additional features and advantages of the present disclosure will be set forth in the detailed description which follows and will be apparent to those skilled in the art from the description, or recognized by practicing the invention as described in the following description, together with the claims and appended drawings.

Figure 1:
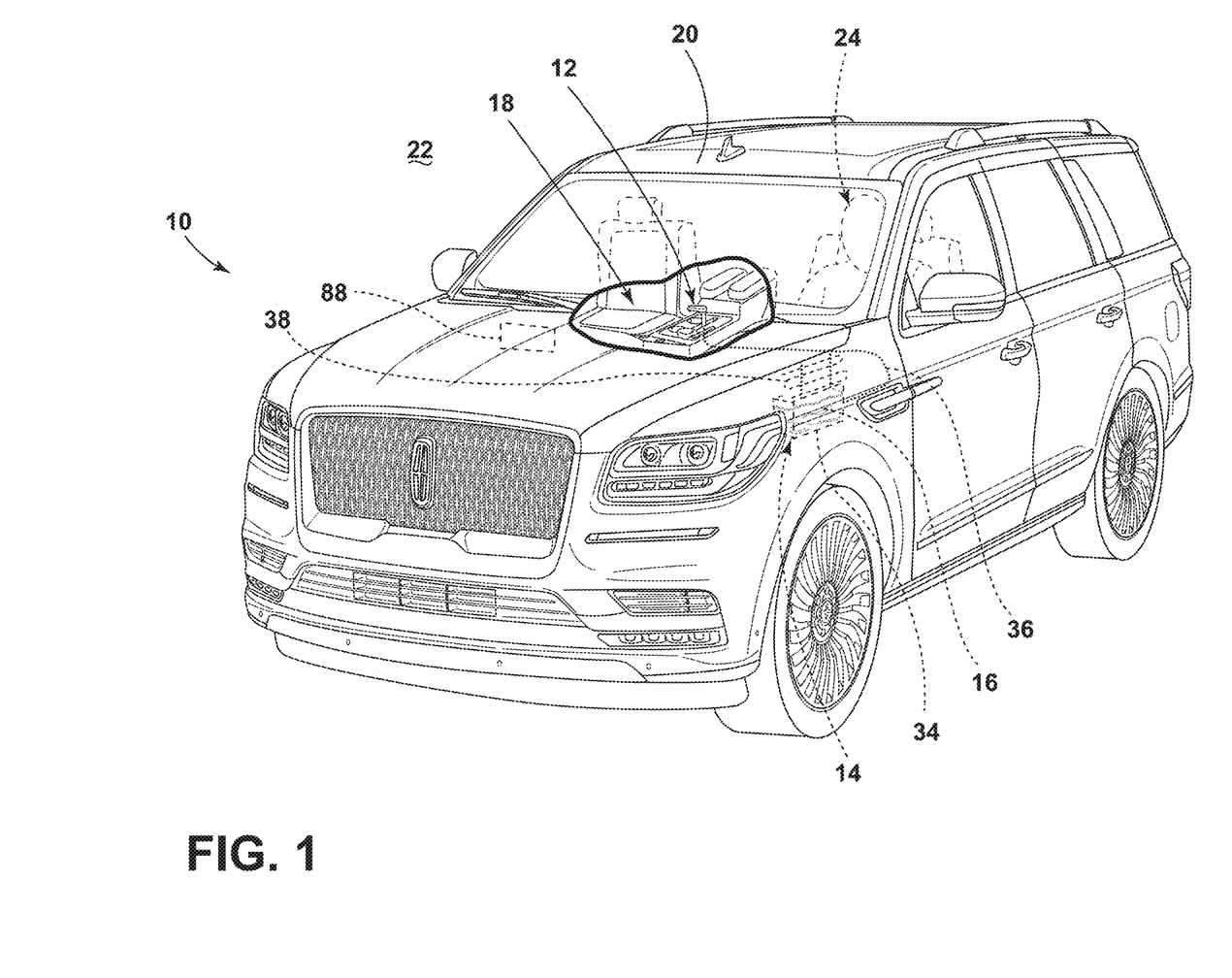
FIG. 1 is a perspective view of a vehicle, illustrating a source of liquid and a liquid dispensing apparatus that can dispense the liquid into an interior of the vehicle.
Figure 2:
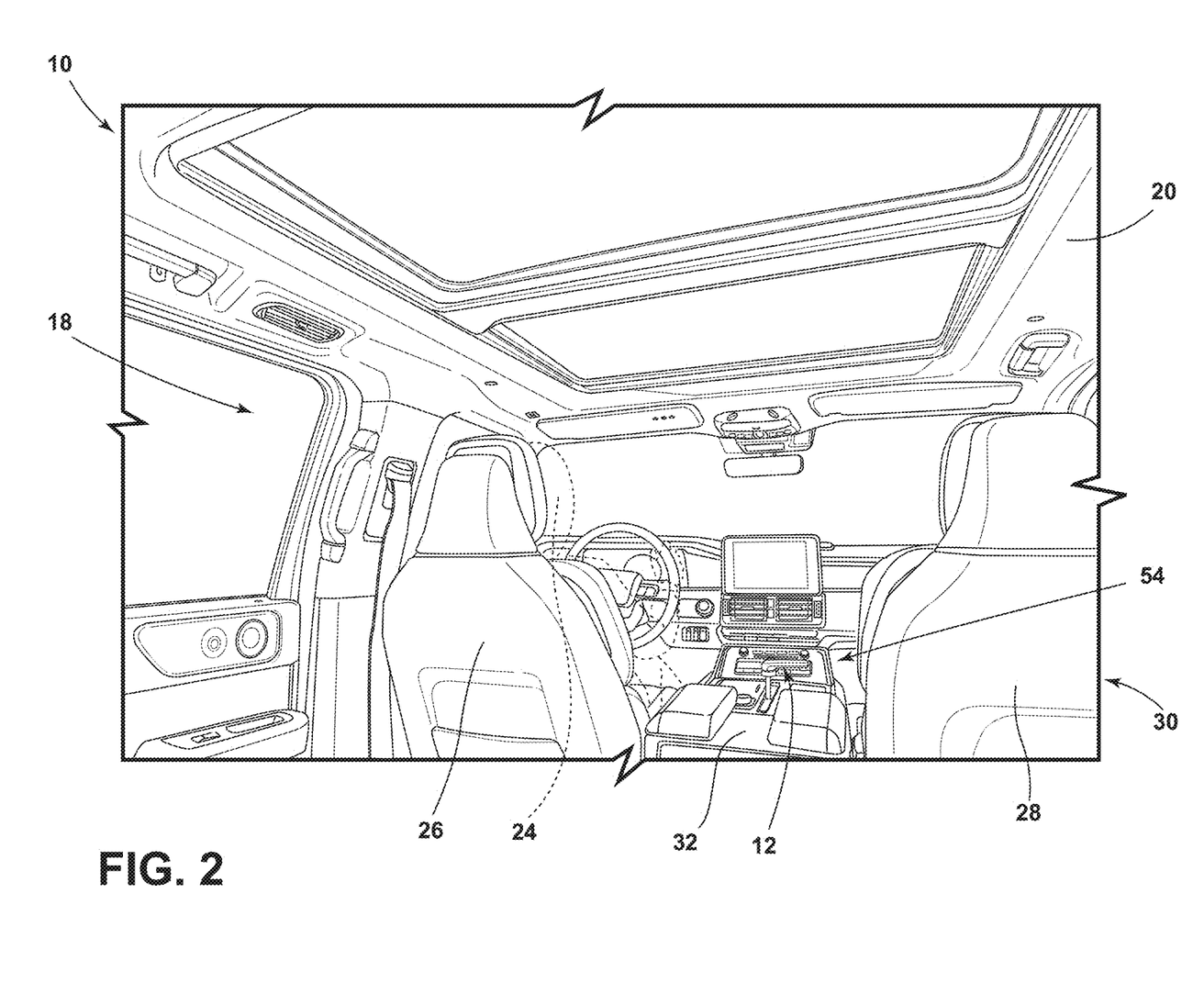
FIG. 2 is a perspective view of the interior of the vehicle of FIG. 1, illustrating the liquid dispensing apparatus disposed at a center console.

Referring now to FIGS. 1 and 2, a vehicle 10 includes a liquid dispensing apparatus 12 and a source 14 of a liquid 16. The vehicle 10 further includes an interior 18 and a body 20 that separates the interior 18 from an external environment 22. The interior 18 is configured for an occupant 24 of the vehicle 10 to occupy. For example, in embodiments, the vehicle 10 further includes a seating assembly 26 on which the occupant 24 can sit while in the vehicle 10. In embodiments, the vehicle 10 further includes another seating assembly 28 that forms a row of seating 30 with the seating assembly 26, and a center console 32 is disposed between the seating assemblies 26, 28. The vehicle 10 can be a car, truck, van, sports utility vehicle, a train rail car, an airplane, a boat, or any other thing that transports the occupant 24. The vehicle 10 can be operated by the occupant 24, semi-autonomous, or fully autonomous. The vehicle 10 can be privately owned. The vehicle 10 can be utilized as part of a ride-hailing or ride-sharing service, with the vehicle 10 transporting occupants 24 of different identity sequentially.

The source 14 of the liquid 16 can be a container 34 that holds the liquid 16. In embodiments, the liquid 16 is water. In embodiments, the liquid 16 comprises water. In embodiments, the liquid 16 is potable and intended for drinking. The source 14 of the liquid 16 is in liquid communication with the liquid dispensing apparatus 12. For example, tubing 36 can provide a flow pathway for the liquid 16 from the source 14 of the liquid 16 to the liquid dispensing apparatus 12.

In embodiments, the vehicle 10 generates the liquid 16. For example, in embodiments, the vehicle 10 collects liquid 16 from an evaporator coil 38 and transports the liquid 16 to the source 14 of the liquid 16. Water vapor from air condenses into water on the evaporator coil 38, and the water is collected and transported to the source 14 as the liquid 16.

Figure 3:
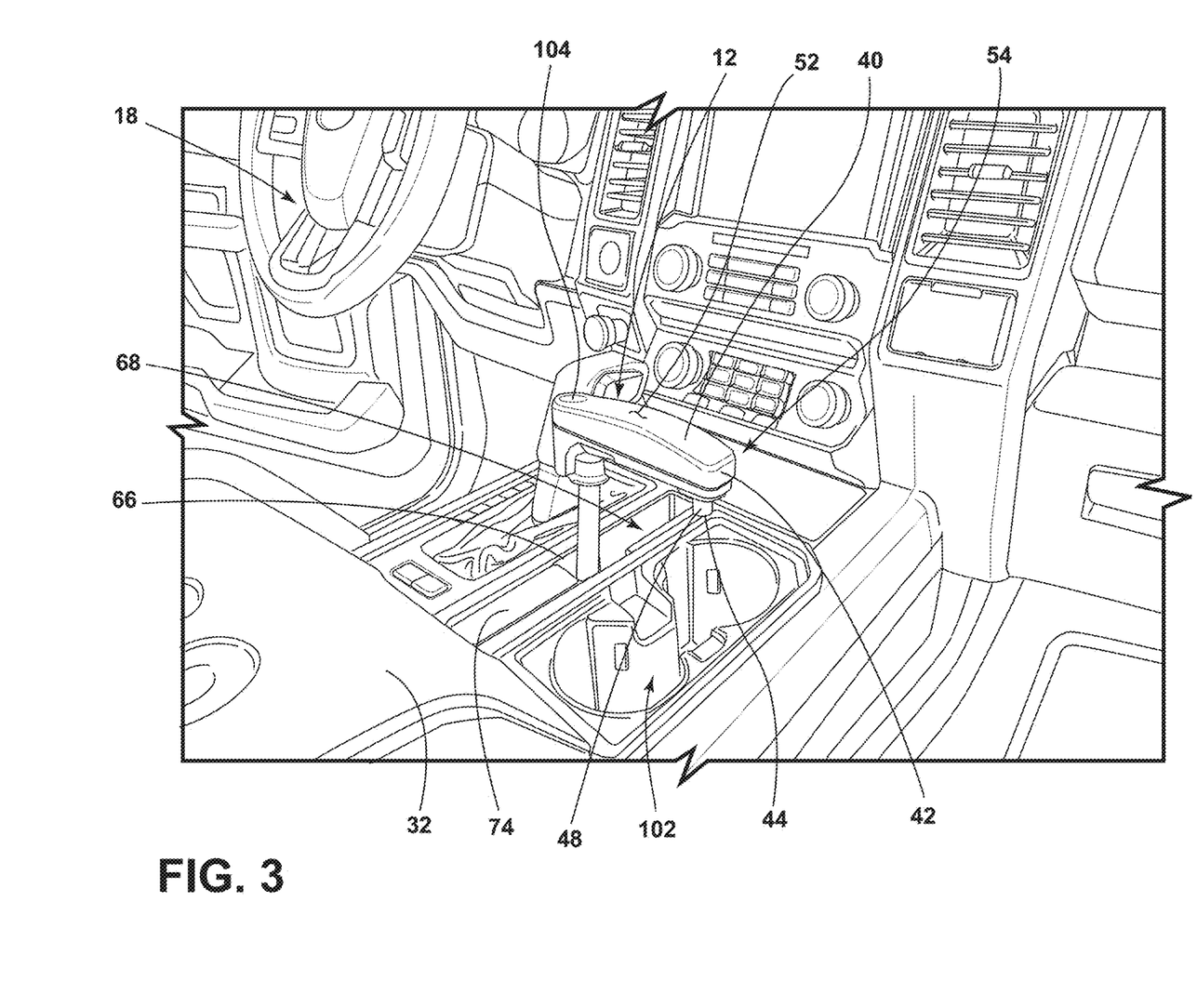
FIG. 3 is a perspective view of the interior of the vehicle of FIG. 1, illustrating the liquid dispensing apparatus including a dispenser in a first position available to dispense the liquid and an outlet projecting from a main body of the dispenser where the liquid would exit the dispenser.

Referring now additionally to FIG. 3, the liquid dispensing apparatus 12 includes a dispenser 40 to dispense the liquid 16. The dispenser 40 is in liquid communication with the source 14 of the liquid 16. The dispenser 40 includes a main body 42, an outlet 44 for the liquid 16, and a conduit 46 leading to the outlet 44. The main body 42 is where the occupant 24 manipulates the dispenser 40 to cause the liquid 16 to dispense out the outlet 44. The conduit 46 extends through the main body 42. The conduit 46 is in liquid communication with the tubing 36 and the outlet 44. The liquid 16 flows from the source 14 of the liquid 16, through the tubing 36, into the conduit 46, and out the outlet 44. The outlet 44 has an outer surface 48 and an inner surface 50.

The liquid 16 contacts the inner surface 50 when the dispenser 40 is dispensing the liquid 16. The outer surface 48 faces in a generally opposite direction as the inner surface 50. The outlet 44 extends from the main body 42, such as in the direction of the intended flow of the liquid 16 when dispensed. In embodiments, the outlet 44 extends downward from the main body 42 but could alternatively extend laterally outward from the main body 42. The main body 42 includes an outer surface 52. In embodiments, the dispenser 40 is accessible from the interior 18 of the vehicle 10, although in other embodiments, the dispenser 40 is available from the external environment 22.

Figure 4:
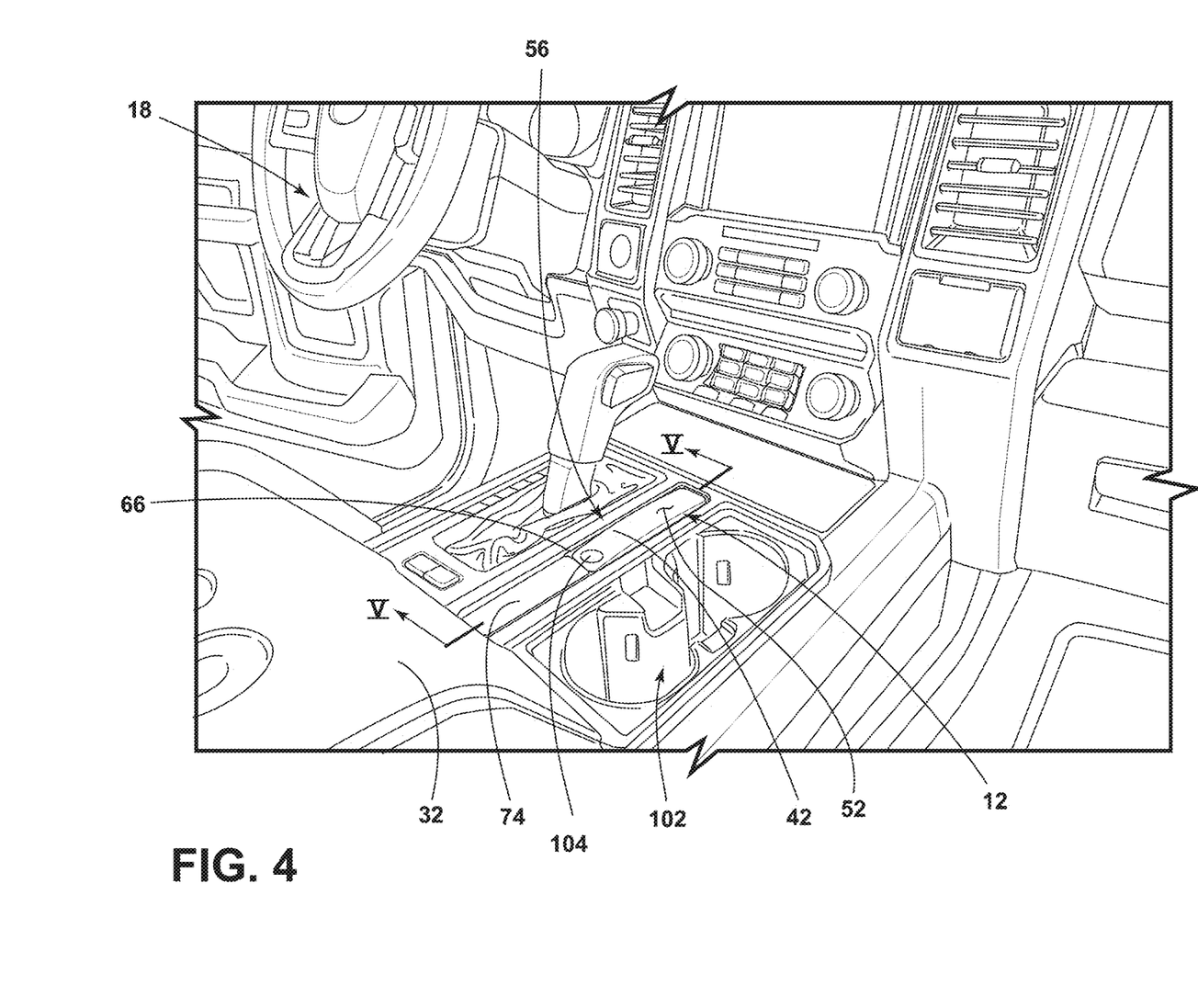
FIG. 4 is a perspective view of a housing at the center console and the dispenser in a second position within the housing.

Referring now additionally to FIG. 4, in embodiments, the dispenser 40 has a first position 54 (see FIG. 3) and a second position 56 (see FIG. 4) that is different than the first position 54. The dispenser 40 can move to, from, and between the first position 54 and the second position 56. For example, the occupant 24 can maneuver the dispenser 40 from the first position 54 to the second position 56, and from the second position 56 to the first position 54. In embodiments, the dispenser 40 is in position to dispense the liquid 16 when the dispenser 40 is in the first position 54.

Figure 5:
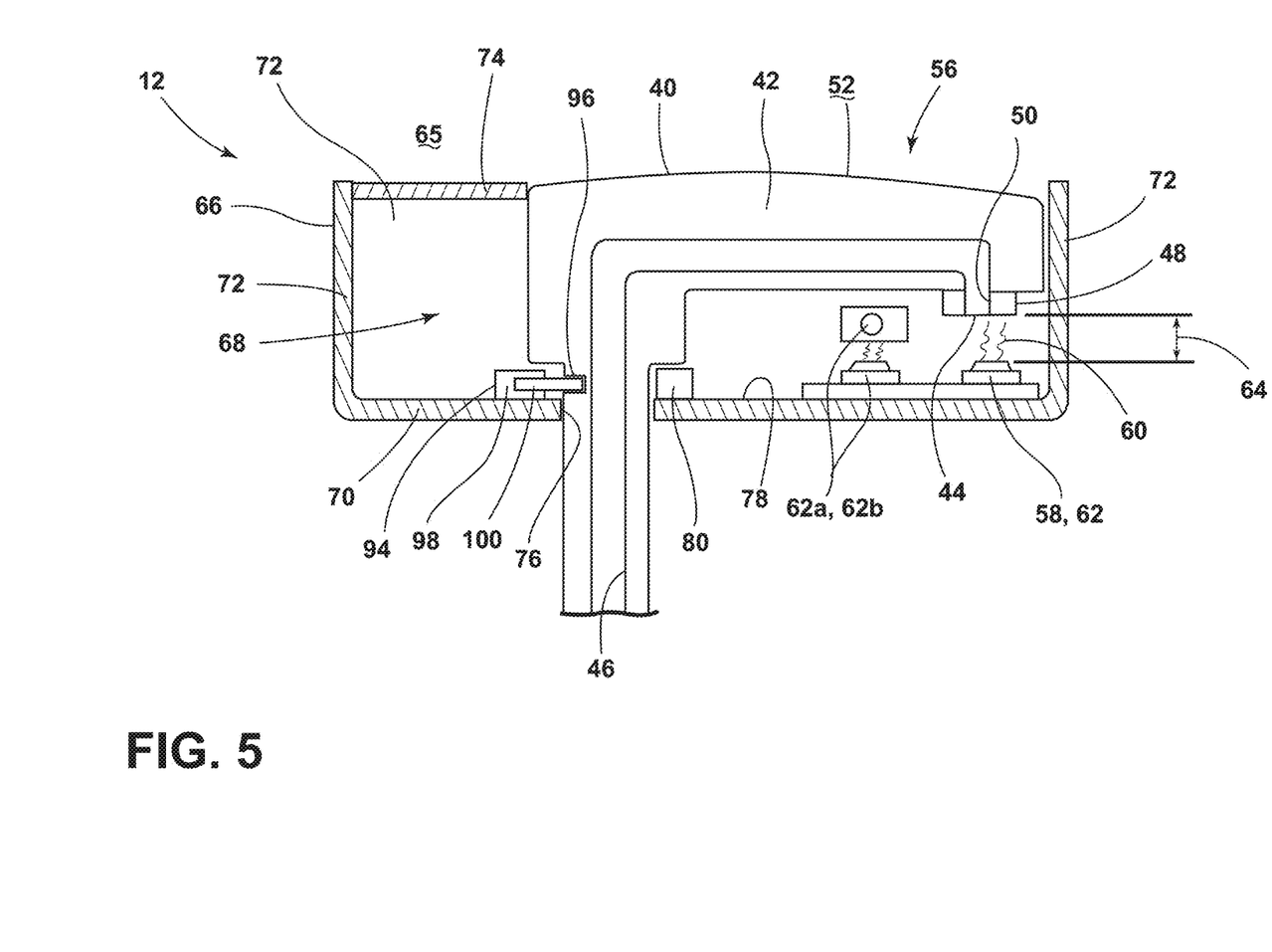
FIG. 5 is an elevational view of the cross-section of the housing of FIG. 4 taken through line V-V of FIG. 4, illustrating the outlet of the dispenser disposed in a chamber that the housing forms, and a source of ultraviolet light emitting the ultraviolet light onto the outlet to sanitize the outlet.

Referring now additionally to FIG. 5, the liquid dispensing apparatus 12 further includes a source 58 of ultraviolet light 60. As used herein, "ultraviolet light" is electromagnetic radiation having a wavelength within a range of from 10 nm to 400 nm. In embodiments, the ultraviolet light 60 that the source 58 emits has a wavelength within a range of from 100 nm to 300 nm. In embodiments, the ultraviolet light 60 has a wavelength within a range of from 240 nm to 300 nm, or within a range of from 250 nm to 280 nm. In embodiments, the source 58 of the ultraviolet light 60 comprises a light emitting diode 62. In embodiments, the source 58 comprises a plurality of light emitting diodes 62, such as light emitting diodes 62, 62a, 62b, . . . 62n as illustrated. In other embodiments, the source 58 comprises a mercury lamp.

The outlet 44 of the dispenser 40 is disposed closer to the source 58 of the ultraviolet light 60 when the dispenser 40 is in the second position 56 than when the dispenser 40 is in the first position 54. For example, in the second position 56, the source 58 of the ultraviolet light 60 is separated by a distance 64. However, in the first position 54, the distance 64 is greater than compared to the second position 56. In embodiments, when the dispenser 40 is in the second position 56, the distance 64 is less than 5 cm, such as 1 mm to 5 cm.

The source 58 of the ultraviolet light 60 is disposed to emit the ultraviolet light 60 onto the outlet 44 of the dispenser 40, at least when the dispenser 40 is in the second position 56. In embodiments, at least when the dispenser 40 is in the second position 56, the source 58 faces the outlet 44 so that the ultraviolet light 60 that the source 58 emits impinges directly upon the outlet 44. In embodiments, the source 58 is disposed vertically below the outlet 44, at least when the dispenser 40 is in the second position 56. In embodiments, the source 58 is disposed in what would be the flow path of the liquid 16, at least when the dispenser 40 is in the second position 56. In embodiments, the ultraviolet light 60 that the source 58 emits impinges upon the inner surface 50 of the outlet 44, at least when the dispenser 40 is in the second position 56. In embodiments, the ultraviolet light 60 that the source 58 emits impinges upon the outer surface 48 of the outlet 44, at least when the dispenser 40 is in the second position 56.

In embodiments, when the dispenser 40 is in the second position 56, the outlet 44 of the dispenser 40 is inaccessible from an environment 65 external to the liquid dispensing apparatus 12. In the context of the liquid dispensing apparatus 12 being an installed component of the vehicle 10, the environment includes the interior 18 that the occupant 24 occupies. In other words, in the second position 56, the outlet 44 of the dispenser 40 is hidden from the view of the occupant 24, and the occupant 24 cannot touch the outlet 44 of the dispenser 40.

In embodiments, the liquid dispensing apparatus 12 further includes a housing 66. The housing 66 at least partially houses the dispenser 40, when the dispenser 40 is in the second position 56. For example, in embodiments, the housing 66 forms a chamber 68. In embodiments, as illustrated, the housing 66 includes a bottom wall 70, side walls 72 extending upward from the bottom wall 70, and optionally a top wall 74. The conduit 46 of the dispenser 40 can extend through an aperture 76 through the bottom wall 70 of the housing 66. When the dispenser 40 is in the second position 56, the bottom wall 70, the side walls 72, and the top wall 74, if present, partially enclose the dispenser 40. The outlet 44 of the dispenser 40 is disposed in the chamber 68, when the dispenser 40 is in the second position 56. When the dispenser 40 is in the second position 56, the bottom wall 70, the side walls 72, and the top wall 74, if present, together with the outer surface 52 of the dispenser 40 enclose the outlet 44 of the dispenser 40 within the chamber 68.

The source 58 of the ultraviolet light 60 is disposed to emit the ultraviolet light 60 into the chamber 68. In embodiments, the source 58 of the ultraviolet light 60 is attached to the housing 66, such as the bottom wall 70 of the housing 66, the side walls 72 of the housing 66, or both the bottom wall 70 and the side walls 72 of the housing 66. In embodiments, the source 58 of the ultraviolet light 60 is disposed at the top wall 74. When the dispenser 40 is in the second position 56, the housing 66 and the outer surface 52 of the main body 42 of the dispenser 40 block the ultraviolet light 60 that the source 58 emits from leaving the chamber 68 to the environment 65 external to the liquid dispensing apparatus 12, such as the interior 18 of the vehicle 10 that the occupant 24 might be occupying. In embodiments, such as that illustrated, the side walls 72 and the top wall 74 of the housing 66 abut the outer surface 52 of the dispenser 40 to prevent escape of the ultraviolet light 60 out of the chamber 68. The ultraviolet light 60 that the source 58 of the ultraviolet light 60 emits does not transmit into the interior 18.

In embodiments, the housing 66 includes a surface 78 that reflects the ultraviolet light 60 that the source 58 of the ultraviolet light 60 emits. In other words, ultraviolet light 60 that the source 58 emits reflects off the surface 78. The surface 78 reflects the ultraviolet light 60 when the surface 78 reflects thirty percent or greater (≥30%) of the ultraviolet light 60 incident to the surface 78. The surface 78 forms at least part of the chamber 68 in which the outlet 44 of the dispenser 40 is disposed when the dispenser 40 is in the second position 56. The surface 78 reflecting the ultraviolet light 60 incident upon the surface 78 increases the intensity of the ultraviolet light 60 that impinges upon the outlet 44, which improves the efficiency of the source 58 of the ultraviolet light 60 sanitizing the outlet 44. The surface 78 that reflects the ultraviolet light 60 can be disposed at the top wall 74.

Figure 6:
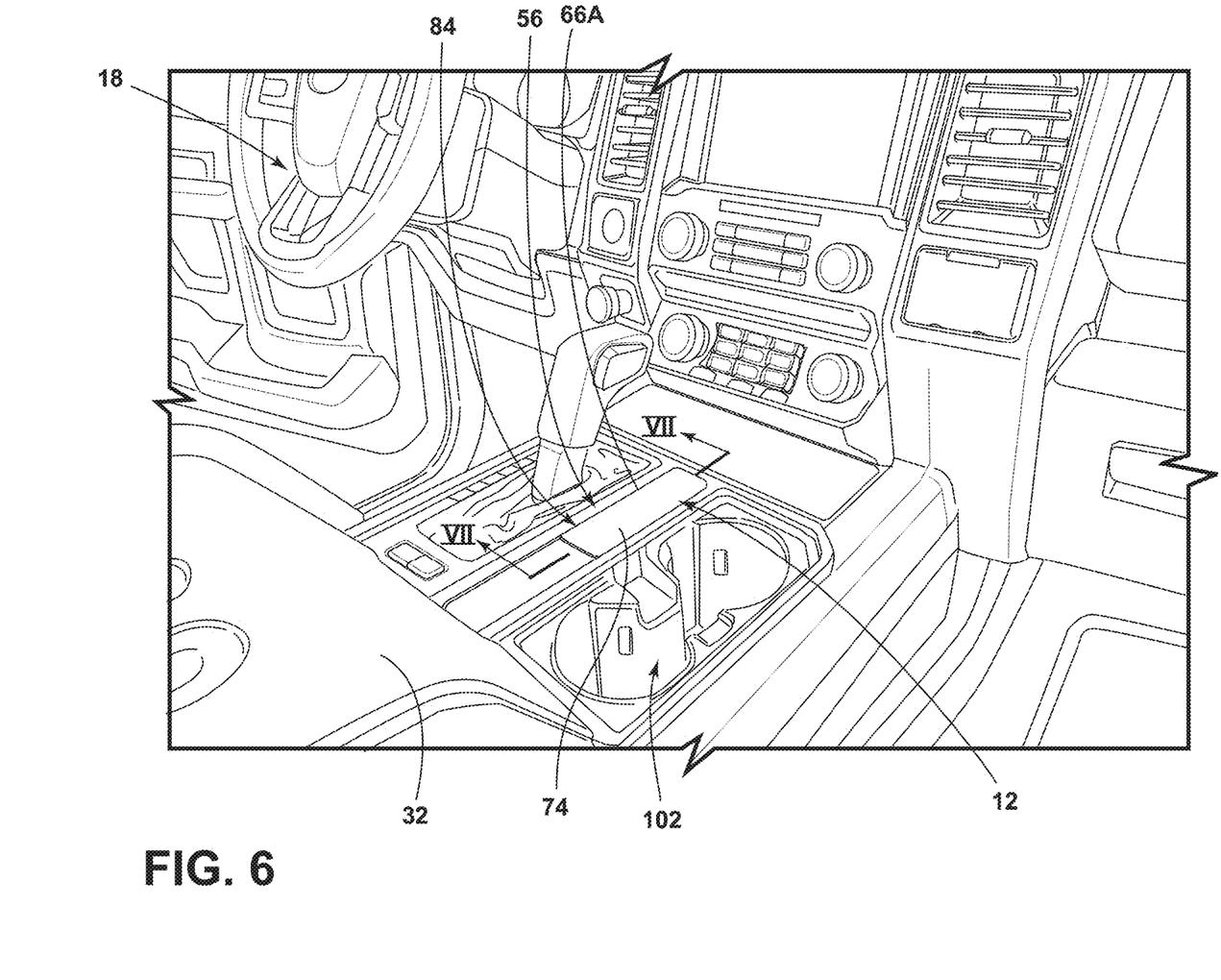
FIG. 6 is the same view as FIG. 4 but showing an alternative embodiment of the housing that has a top wall that extends over the dispenser when the dispenser is in the chamber of the housing.
Figure 7:
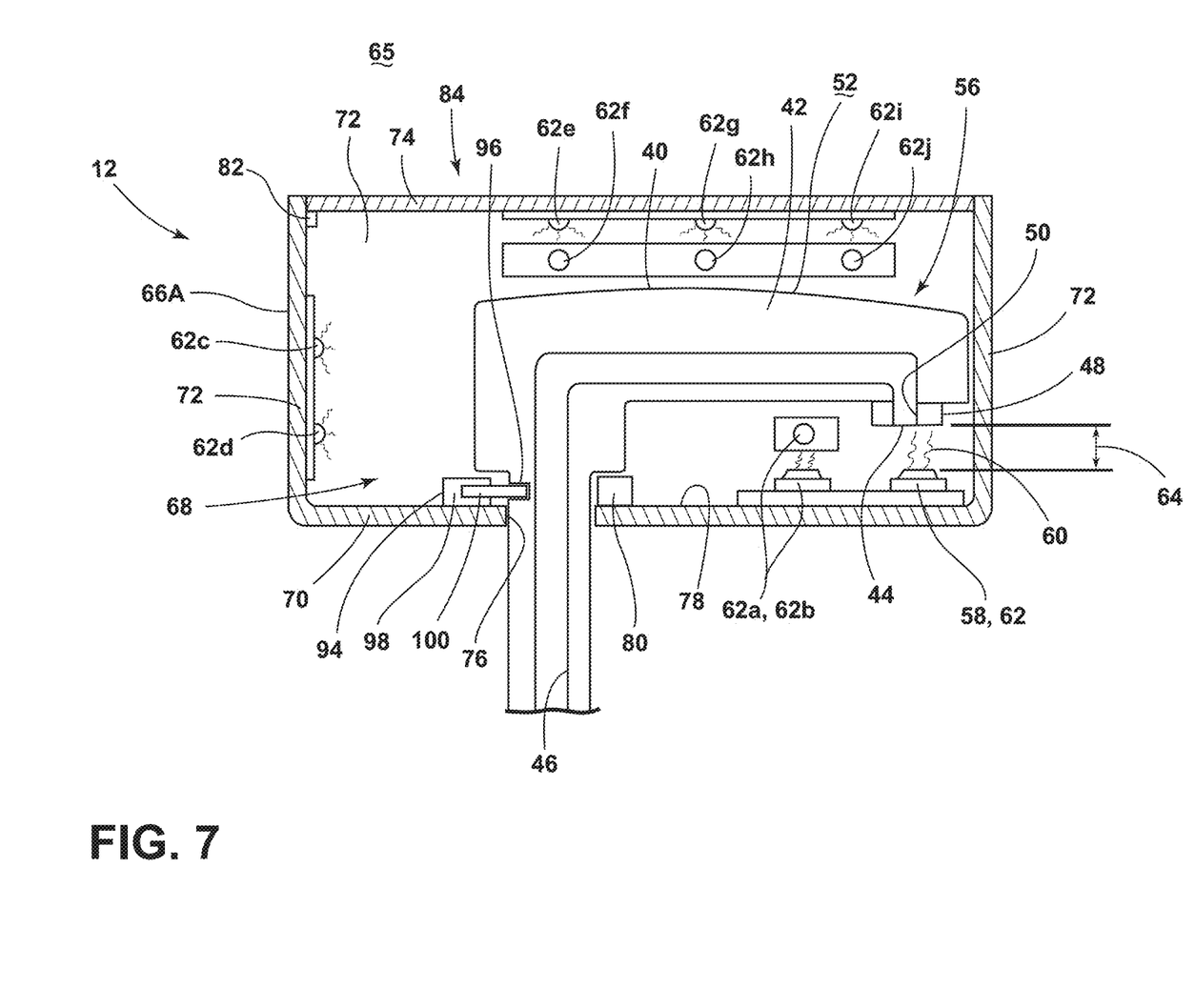
FIG. 7 is an elevational view of the cross-section of the alternative embodiment housing of FIG. 6 taken through line VII-VII of FIG. 6, illustrating the main body as well as the outlet disposed in the chamber of the housing and the top wall of the housing extending over the main body of the dispenser.

Referring now to FIGS. 6 and 7, in an alternative embodiment, a housing 66A completely houses the dispenser 40, when the dispenser 40 is in the second position 56. For example, the top wall 74 of the housing 66A can extend entirely over the main body 42 of the dispenser 40, when the dispenser 40 is in the second position 56. Thus, the top wall 74, the side walls 72, and the bottom wall 70 of the housing 66A form the chamber 68 and entirely encloses the dispenser 40 within the chamber 68, except for the aperture 76 through the bottom wall 70. In embodiments, the top wall 74 is movable to allow the dispenser 40 to move to, from, and between the first position 54 and the second position 56. For example, the top wall 74 can be retractable relative to the side walls 72 or hinged to the side walls 72 as a lid (as in the illustrated embodiment). The source 58 of the ultraviolet light 60 is configured to emit the ultraviolet light 60 onto the entirety of the outer surface 52 of the main body 42 of the dispenser 40. For example, the source 58 of the ultraviolet light 60 within the housing 66A can include additional light emitting diodes 62c-62j or other emitters of the ultraviolet light 60 higher than the dispenser 40, such as at the top wall 74 or the side walls 72 near the top wall 74, so that the ultraviolet light 60 is emitted onto the entirety of the outer surface 52 of the main body 42 of the dispenser 40. Thus, the liquid dispensing apparatus 12 sanitizes the entirety of the dispenser 40 that the occupant 24 can touch, which further reduces the ability of the dispenser 40 to operate as a vector to transport microbes from the dispenser 40 to the liquid 16 that the dispenser 40 dispenses. The housing 66A is otherwise identical to the housing 66.

In embodiments, the liquid dispensing apparatus 12 further includes a sensor 80. The sensor 80 is configured to output data that changes as a function of whether the dispenser 40 is in the second position 56. In other words, the sensor 80 generates an output when the dispenser 40 is in the second position 56 that is different than an output that the sensor 80 generates when the dispenser 40 is not in the second position 56, such as in the first position 54 or moving to the first position 54. The sensor 80 can be a light sensor, a proximity sensor, among other options. In addition, the sensor 80 can be a switch that closes an electrical circuit to the source 58 of the ultraviolet light 60 only when the dispenser 40 is in the second position 56.

In embodiments that include the housing 66A with the top wall 74 that is openable, the liquid dispensing apparatus 12 further includes a sensor 82. The sensor 82 is configured to output data that changes as a function of whether the top wall 74 is in a closed position 84. In other words, the sensor 82 generates an output when the top wall 74 is in the closed position 84 that is different than an output that the sensor 82 generates when the top wall 74 is not in the closed position 84, such as in an open position 86 (see FIG. 9B) or moving to the open position 86. When the top wall 74 is in the open position 86, the dispenser 40 is able to move to, from, and between the first position 54 and the second position 56. The sensor 82 can be a light sensor, a proximity sensor, among other options. In addition, sensor 82 can be a switch that closes an electrical circuit to the source 58 of the ultraviolet light 60 only when the top wall 74 is in the closed position 84.

Figure 8:
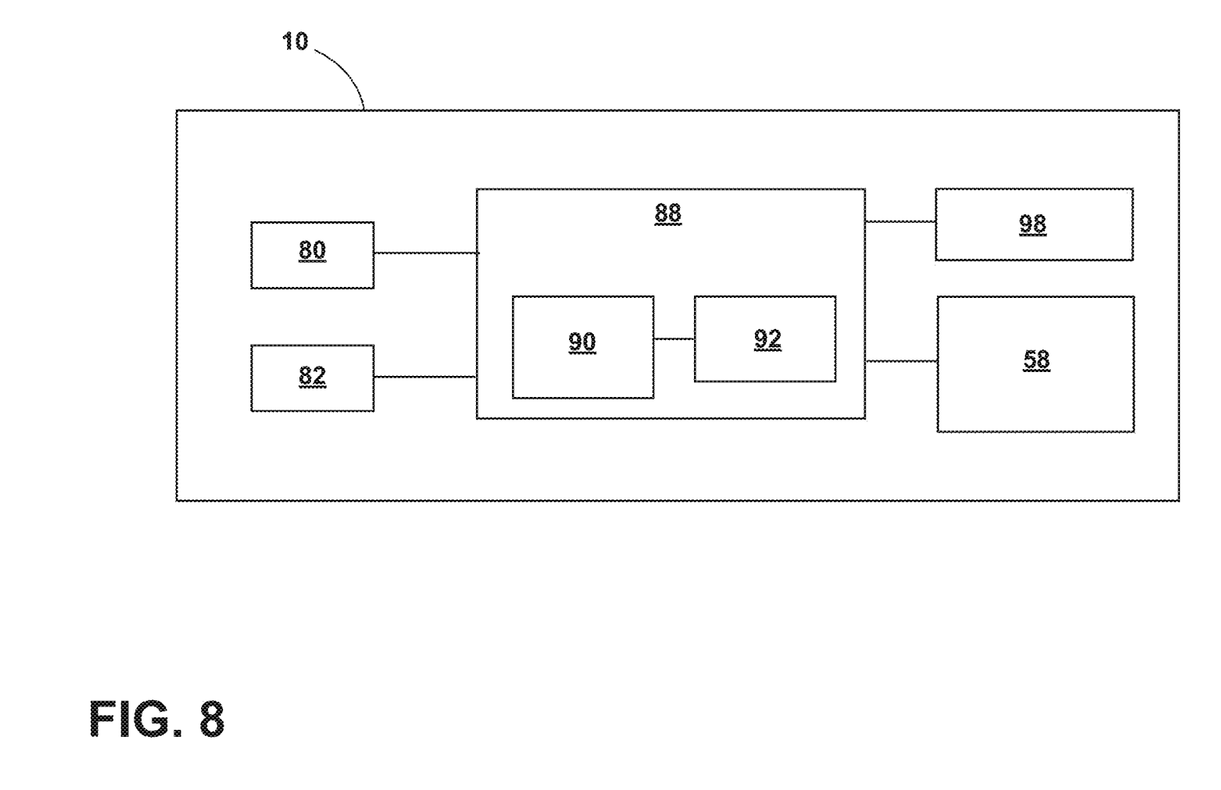
FIG. 8 is a schematic view of a controller of the vehicle, illustrating the controller in communication with (i) the source of the ultraviolet light and (ii) sensors to ensure that the dispenser is in the second position within the chamber of the housing and, in embodiments, that the top wall is in a closed position.

In embodiments, referring now additionally to FIG. 8, the vehicle 10 further includes a controller 88 that is in communication with the source 58 of the ultraviolet light 60, the sensor 80 that determines the position of the dispenser 40, and the sensor 82 that determines the position of the top wall 74 of the housing 66. The controller 88 controls activation and deactivation of the source 58 of the ultraviolet light 60. When the controller 88 activates the source 58 of the ultraviolet light 60, the source 58 emits the ultraviolet light 60. When the controller 88 deactivates the source 58 of the ultraviolet light 60, the source 58 does not emit the ultraviolet light 60. The sensor 80 outputs data to the controller 88. In embodiments, when the sensor 80 outputs data indicative of the dispenser 40 being in the second position 56, the controller 88 activates the source 58 of the ultraviolet light 60. In embodiments where the housing 66A includes the top wall 74 that is movable, when the sensor 80 outputs data indicative of the dispenser 40 being in the second position 56 and the sensor 82 outputs data indicative of the top wall 74 being in the closed position 84, the source 58 emits the ultraviolet light 60. In embodiments, when the sensor 80 outputs data indicative of the dispenser 40 not being in the second position 56, or the sensor 82 outputs data indicative of the top wall 74 not being in the closed position 84, the controller 88 deactivates the source 58 of the ultraviolet light 60. In other words, as a function of data received from the sensor 80 and the sensor 82, the controller 88 causes the source 58 to emit the ultraviolet light 60 when the dispenser 40 is in the second position 56 but not when the dispenser 40 is in the first position 54 (or away from the second position 56) or the top wall 74 is in the open position 86 (or away from the closed position 84). The controller 88 deactivating the source 58 of the ultraviolet light 60 when the sensor 82 provides output indicating the top wall 74 not being in the closed position 84 prevents emission of the ultraviolet light 60 outside of the housing 66 and into the interior 18 of the vehicle 10. For example, if the occupant 24 were to move the top wall 74 of the housing 66 to or toward the open position 86, the sensor 82 provides data indicating such to the controller 88 and the controller 88 deactivates the source 58 of the ultraviolet light 60. The controller 88 deactivating the source 58 of the ultraviolet light 60 when the sensor 82 provides output indicating the dispenser 40 not being in the second position 56 prevents emission of the ultraviolet light 60 into the interior 18 of the vehicle 10 in embodiments where the main body 42 of the dispenser 40 forms part of the chamber 68 enclosing the outlet 44 of the dispenser 40.

The controller 88 includes a processor 90 and memory 92. The memory 92 can store programs to effectuate activation and deactivation of the source 58 of the ultraviolet light 60 based on data received from the sensor 80 and the sensor 82. The processor 90 executes the programs. The processor 90 may be any suitable processing device or set of processing devices such as, but not limited to, a microprocessor, a microcontroller-based platform, an integrated circuit, one or more field programmable gate arrays (FPGAs), and/or one or more application-specific integrated circuits (ASICs). The memory 92 may be volatile memory (e.g., RAM including non-volatile RAM, magnetic RAM, ferroelectric RAM, etc.), non-volatile memory (e.g., disk memory, FLASH memory, EPROMs, EEPROMs, memristor-based non-volatile solid-state memory, etc.), unalterable memory (e.g., EPROMs), read-only memory, and/or high-capacity storage devices (e.g., hard drives, solid-state drives, etc.). In some examples, the memory 92 includes multiple kinds of memory, particularly volatile memory and non-volatile memory.

In embodiments, the liquid dispensing apparatus 12 further includes a locking mechanism 94. The locking mechanism 94 prevents the dispenser 40 from moving away from the second position 56 while the source 58 of the ultraviolet light 60 is emitting the ultraviolet light 60. After the source 58 has been deactivated and is no longer emitting the ultraviolet light 60, the locking mechanism 94 no longer prevents the dispenser 40 from moving away from the second position 56. In embodiments, the locking mechanism 94 includes a keyhole 96 into the dispenser 40 and an actuator 98 to position selectively a key 100 into or out of the keyhole 96. The actuator 98 is in communication with the controller 88. When the controller 88 activates the source 58 of the ultraviolet light 60, the controller 88 additionally actuates the actuator 98 to move the key 100 into the keyhole 96 of the dispenser 40. When the controller 88 deactivates the source 58 of the ultraviolet light 60, the controller 88 additionally actuates the actuator 98 to withdraw the key 100 from the keyhole 96 of the dispenser 40, which allows the occupant 24 to move the now-sanitized dispenser 40 from the second position 56 to the first position 54 to dispense the liquid 16.

As mentioned, the dispenser 40 can be accessible from the interior 18 of the vehicle 10. In embodiments, the dispenser 40 and the housing 66, 66A are disposed at the center console 32. The center console 32 can further include a cup holder 102 adjacent to the housing 66, 66A. In other embodiments, the dispenser 40 and the housing 66, 66A are disposed at another place within the interior 18 of the vehicle 10. In embodiments, the dispenser 40 and the housing 66, 66A are available for use from the external environment 22 outside of the vehicle 10.

Figure 9A:
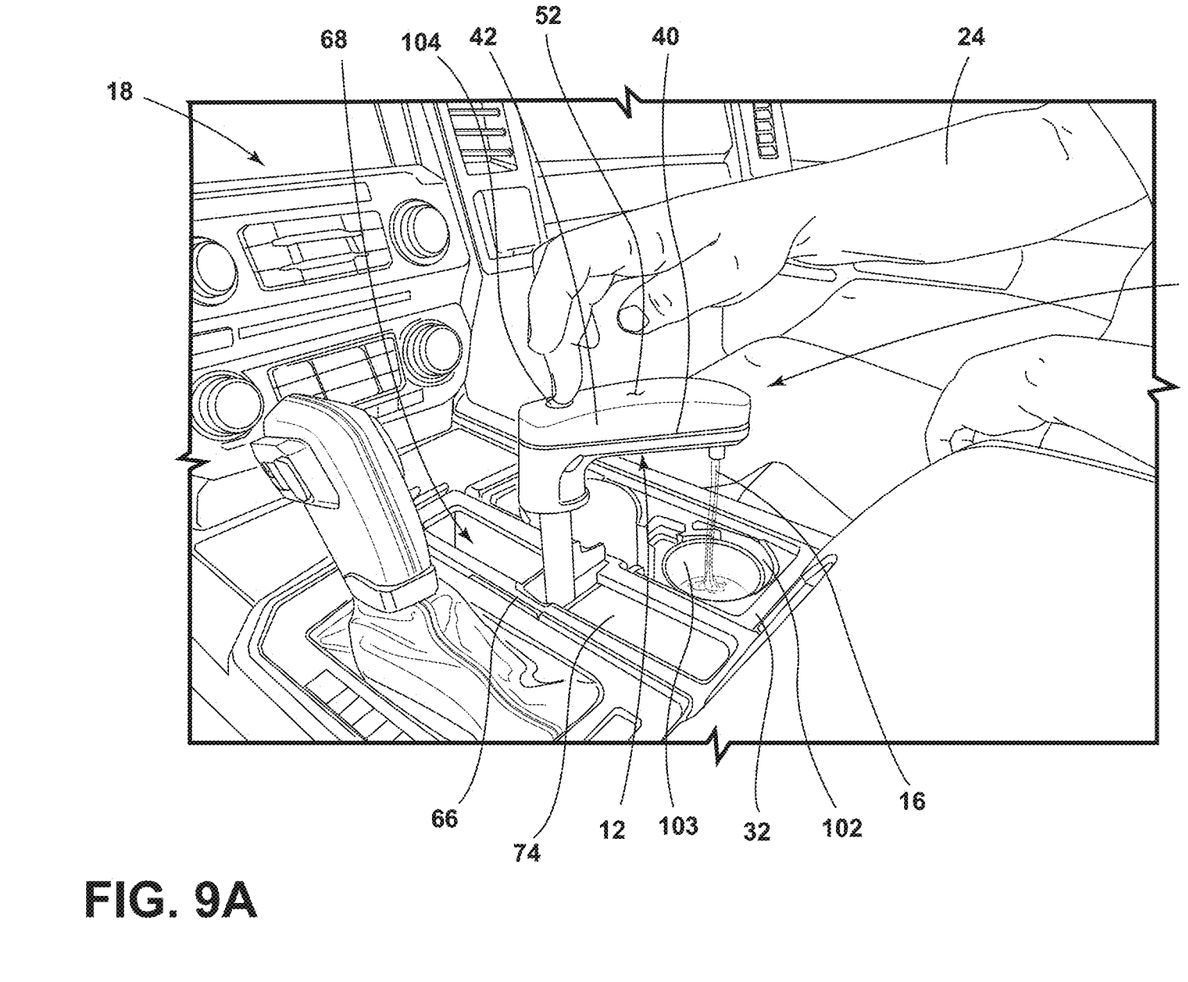
FIG. 9A is a perspective view of the dispenser in the first position dispensing liquid into a cup within a cup holder at the center console.
Figure 9B:
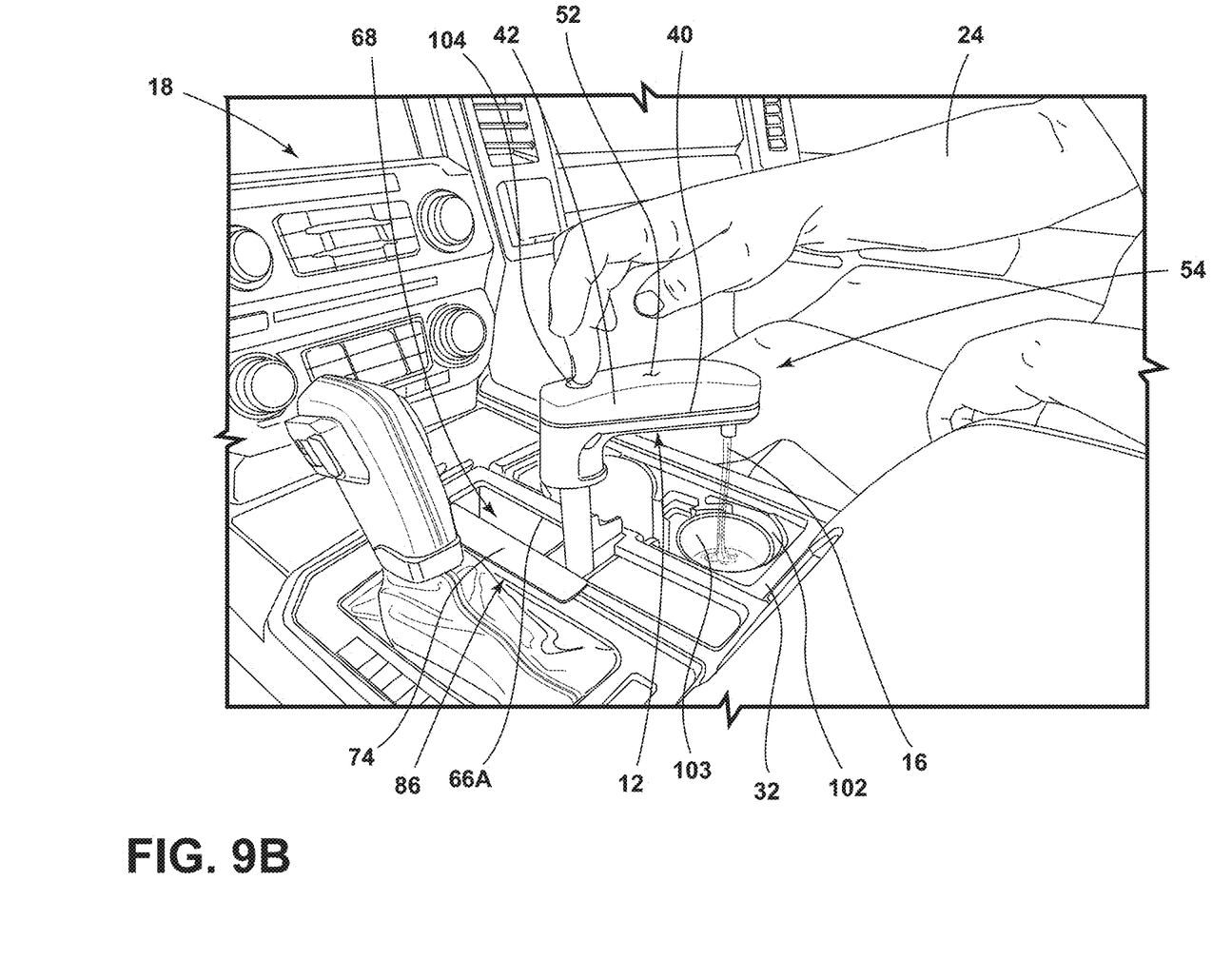
FIG. 9B is a perspective view of the alternative embodiment housing of FIG. 6 with the top wall in an open position and the dispenser in the first position dispensing liquid.

In use, referring now additionally to FIGS. 9A and 9B, the occupant 24 can place the dispenser 40 in the first position 54 with the outlet 44 of the dispenser 40 vertically above a cup 103 (such as the cup 103 in the cup holder 102). In embodiments with the housing 66A, the occupant initially moves the top wall 74 from the closed position 84 (see FIG. 6) to the open position 86 (see FIG. 9B), before placing the dispenser 40 in the first position 54. The occupant 24 can then direct the dispenser 40 to dispense the liquid 16 out of the outlet 44 and into the cup 103, such as by pressing a button 104. The button 104 may open a valve (not illustrated) allowing the liquid 16 to proceed through the conduit 46.

After the occupant 24 has completed dispensing the liquid 16, the occupant 24 then moves the dispenser 40 from the first position 54 to the second position 56. In embodiments with the housing 66A, the occupant moves the top wall 74 from the open position 86 to the closed position 84, and the sensor 82 senses so and informs the controller 88. Further, the sensor 80 senses that the dispenser 40 is in the second position 56, informs the controller 88, and the controller 88 activates the source 58 of the ultraviolet light 60.

The source 58 then emits the ultraviolet light 60 onto the outlet 44 of the dispenser 40. In embodiments, the controller 88 activates the source 58 only after a predetermined period of time has elapsed since the controller 88 has received information that the dispenser 40 is in the second position 56, and the top wall 74 of the housing 66A is in the second position 56. The predetermined period of time can be, for example, 60 seconds. In embodiments, the controller 88 causes the actuator 98 to move the key 100 into the keyhole 96 of the dispenser 40, before causing the source 58 to emit the ultraviolet light 60.

After the controller 88 activates the source 58, the surface 78 of the housing 66 reflects the ultraviolet light 60, which increases the amount of the ultraviolet light 60 that interacts with the other surfaces of the dispenser 40 exposed to the ultraviolet light 60, to reduce or eliminate microbes present the other surfaces. In embodiments, the controller 88 activates the source 58 of the ultraviolet light 60 for a preset period of time, such as 1 second, 5 seconds, 30 seconds, 1 minute, 2 minutes, 3 minutes, 4 minutes, 5 minutes, 6 minutes, 7 minutes, 8 minutes, 9 minutes, 10 minutes, 30 minutes, 1 hours, or any range between any two of those values (e.g., 3 minutes to 30 minutes, 4 minutes to 8 minutes, and so on). The ultraviolet light 60 does not leave the chamber 68, because the housing 66A or the housing 66 together with the outer surface 52 of the main body 42 of the dispenser 40 blocks the ultraviolet light 60. Thus, the emission of the ultraviolet light 60 can occur while the occupant 24 occupies the interior 18. After the preset period of time has expired, the controller 88 deactivates the source 58 of the ultraviolet light 60.

In the event that the controller 88 receives information that the dispenser 40 is no longer in the second position 56, or the top wall 74 of the housing 66A is no longer in the second position 56, then the controller 88 deactivates the source 58 to halt emission of the ultraviolet light 60.

In embodiments, the controller 88 monitors a period of time that has expired since the controller 88 last activated the source 58 of the ultraviolet light 60 to sanitize the outlet 44 of the dispenser 40. If (i) the period of time is greater than a preset period of time (e.g., 72 hours), (ii) the sensor 80 provides data indicative of the dispenser 40 being in the second position 56, and, for housing 66A, (iii) the sensor 82 provides data indicative of the top wall 74 being in the closed position 84, then the controller 88 activates the source 58 of the ultraviolet light 60 to again sanitize the outlet 44 of the dispenser 40. In embodiments, the controller 88 activates the source 58 when the vehicle 10 is next started.

Figure 10:
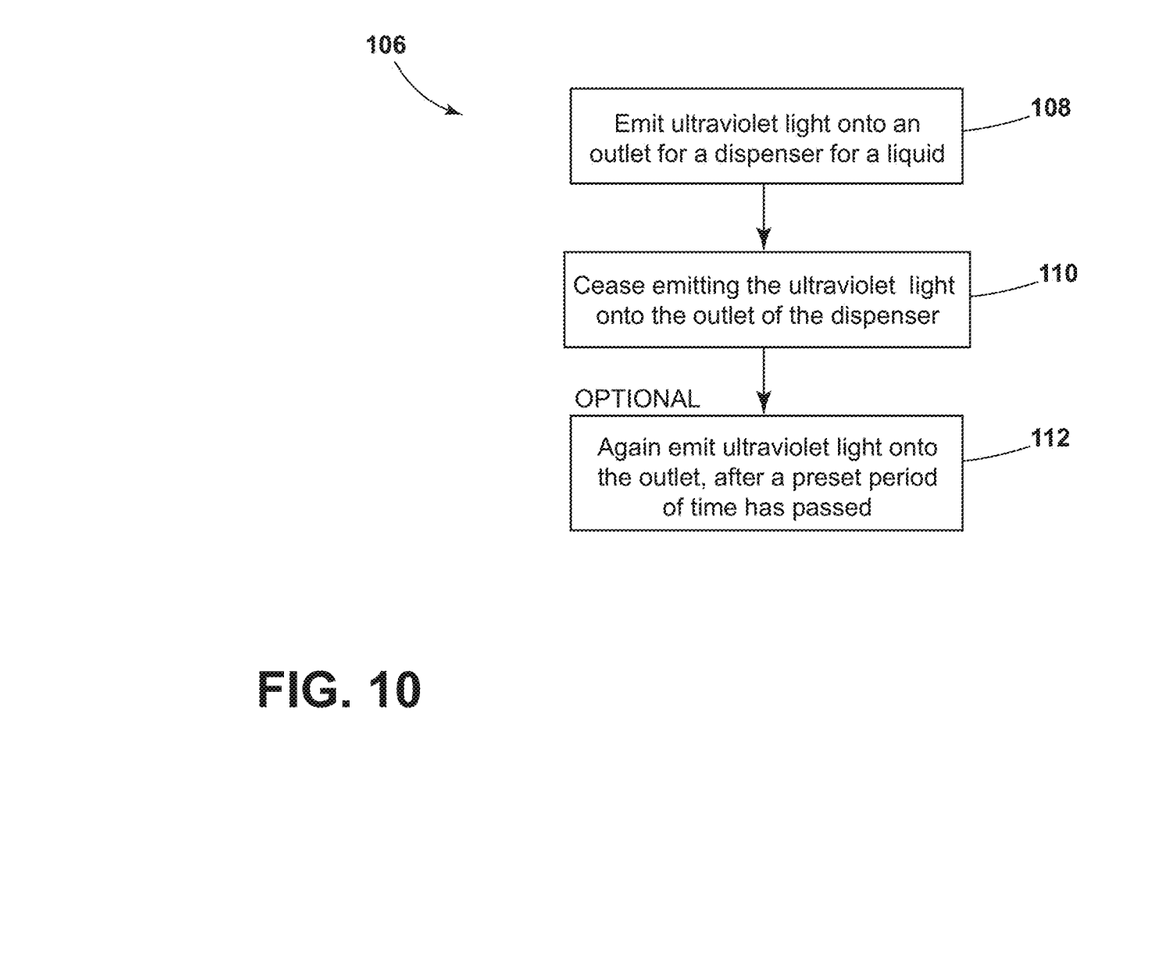
FIG. 10 is a schematic view of a method of sanitizing the dispenser via emitting the ultraviolet light onto the dispenser.

Referring now to FIG. 10, a method 106 of sanitizing the dispenser 40 for the liquid 16 is herein disclosed. At a step 108, the method 106 includes emitting the ultraviolet light 60 onto the outlet 44 of the dispenser 40 for the liquid 16. In embodiments, step 108 comprises emitting the ultraviolet light 60 onto the entirety of the outer surface 52 of the main body 42 of the dispenser 40. As discussed, in embodiments, the step 108 occurs as a consequence of the dispenser 40 moving from the first position 54 to the second position 56. At a step 110, the method 106 further includes ceasing emitting the ultraviolet light 60 onto the outlet 44 of the dispenser 40. As discussed, in embodiments, the controller 88 deactivates the source 58 of the ultraviolet light 60 after a preset period of time or upon receiving data from (i) the sensor 80 indicating that the dispenser 40 is not in the second position 56 or (ii) the sensor 82 indicating that the top wall 74 is not in the closed position 84.

In embodiments, the method 106 further includes, at a step 112, again emitting the ultraviolet onto the outlet 44 of the dispenser 40, after a preset period of time has passed. As mentioned above, even in the second position 56, the outlet 44 of the dispenser 40 might encounter microbes that deposit on the outlet 44. To maintain sanitization of the outlet 44, the controller 88 causes periodic sanitization of the outlet 44 by activating the source 58 of the ultraviolet light 60.

The emission of the ultraviolet light 60 onto the outlet 44 of the dispenser 40, or the dispenser 40 entirely including the main body 42 and the outlet 44, reduces or eliminates microbes present thereupon. When the occupant 24 subsequently utilizes the dispenser 40 to dispense the liquid 16, the outlet 44 or the dispenser 40 entirely including the main body and the outlet 44 does not transfer the microbes to the liquid 16. The liquid 16 is thus dispensed in its existing sterility state, without contamination from the outlet 44. Because the ultraviolet light 60 sanitizes the dispenser 40, the use of physical cleaning agents are unnecessary. Because the controller 88 activates the source 58 without command from the occupant 24, the dispenser 40 is nearly perpetually in a sanitized state.

It is to be understood that variations and modifications can be made on the aforementioned structure without departing from the concepts of the present invention, and further it is to be understood that such concepts are intended to be covered by the following claims unless these claims by their language expressly state otherwise.

What is claimed is:

1. A liquid dispensing apparatus for a vehicle comprising:
a dispenser comprising (i) an outlet for a liquid, (ii) a main body comprising an outer surface, (iii) a conduit extending through the main body, the conduit being in liquid communication with the outlet, (iv) a first position and (v) a second position that is different than the first position;
a source of ultraviolet light disposed to emit the ultraviolet light onto the outlet of the dispenser; and
a housing that form a chamber in which the outlet of the dispenser is disposed when the dispenser is in the second position, the housing comprising a movable top wall that (i) extends over the main body the dispenser, when the dispenser is in the second position, and (ii) forms part of the chamber in which the outlet of the dispenser is disposed when the dispenser is in the second position,
wherein, the source of the ultraviolet light is disposed to emit the ultraviolet light into the chamber, and
wherein, the outlet of the dispenser is disposed closer to the source of the ultraviolet light when the dispenser is in the second position than when the dispenser is in the first position.

2. The liquid dispensing apparatus of claim 1, wherein the dispenser is in position to dispense the liquid when the dispenser is in the first position.

3. The liquid dispensing apparatus of claim 1, wherein in the second position, the outlet of the dispenser is inaccessible from an environment external to the liquid dispensing apparatus.

4. The liquid dispensing apparatus of claim 1, wherein the dispenser can move to, from, and between the first position and the second position.

5. The liquid dispensing apparatus of claim 1, wherein the housing comprises a surface forming at least part of the chamber, and the surface reflects the ultraviolet light that the source of the ultraviolet light emits.

6. The liquid dispensing apparatus of claim 1, wherein the source of the ultraviolet light is configured to emit the ultraviolet light onto an entirety of the outer surface of the main body of the dispenser.

7. The liquid dispensing apparatus of claim 1 further comprising:
a sensor configured to output data that changes as a function of whether the dispenser is in the second position.

8. The liquid dispensing apparatus of claim 1, wherein the dispenser is configured to be in liquid communication with a source of the liquid that is disposed within the vehicle.

9. A vehicle comprising:
a center console;
a dispenser for a liquid, the dispenser comprising (i) an outlet for the liquid, (ii) a first position, and (iii) a second position that is different than the first position;
a housing disposed at the center console, the housing comprising a chamber in which the outlet of the dispenser is disposed when the dispenser is in the second position; and
a source of ultraviolet light disposed to emit the ultraviolet light into the chamber and onto the outlet of the dispenser when the dispenser is in the second position.

10. The vehicle of claim 9, wherein
the outlet of the dispenser is disposed closer to the source of the ultraviolet light when the dispenser is in the second position than when the dispenser is in the first position.

11. The vehicle of claim 9 further comprising:
a controller in communication with the source of the ultraviolet light, the controller causing the source of ultraviolet light to emit the ultraviolet light when the dispenser is in the second position but not when the dispenser is in the first position.

12. The vehicle of claim 11 further comprising:
a sensor in communication with the controller, the sensor configured to output data that changes as a function of whether the dispenser is in the second position;
wherein, the controller causes the source of the ultraviolet light to emit the ultraviolet light when the sensor outputs data indicative that the dispenser is in the second position.

13. The vehicle of claim 9, wherein
the dispenser can move to, from, and between the first position and the second position.

14. The vehicle of claim 9, wherein
the housing comprises a surface forming at least part of the chamber, and the surface reflects the ultraviolet light that the source of the ultraviolet light emits.

15. The vehicle of claim 9 further comprising:
a source of the liquid in liquid communication with the dispenser.

16. The vehicle of claim 15, wherein
the vehicle generates the liquid that the dispenser dispenses.

17. The vehicle of claim 9, wherein
the dispenser is in position to dispense the liquid when the dispenser is in the first position.

18. The vehicle of claim 9, wherein
the dispenser further comprises a main body and a conduit extending through the main body, the main body comprising an outer surface, and the conduit being in liquid communication with the outlet;
the housing comprises a movable top wall that (i) extends over the main body of the dispenser, when the dispenser is in the second position, and (ii) forms part of the chamber in which the outlet of the dispenser is disposed when the dispenser is in the second position; and
the source of the ultraviolet light is configured to emit the ultraviolet light onto an entirety of the outer surface of the main body of the dispenser.

19. A vehicle comprising:
a dispenser comprising (i) an outlet for a liquid, (ii) a main body comprising an outer surface, (iii) a conduit extending through the main body, the conduit being in liquid communication with the outlet, (iv) a first position, and (v) a second position that is different than the first position;
a source of ultraviolet light disposed to emit the ultraviolet light onto the outlet of the dispenser; and
a housing that forms a chamber in which the outlet of the dispenser is disposed when the dispenser is in the second position, the housing comprising a movable top wall that (i) extends over the main body of the dispenser, when the dispenser is in the second position, and (ii) forms part of the chamber in which the outlet of the dispenser is disposed when the dispenser is in the second position,
wherein, the source of the ultraviolet light is disposed to emit the ultraviolet light into the chamber, and wherein, the outlet of the dispenser is disposed closer to the source of the ultraviolet light when the dispenser is in the second position than when the dispenser is in the first position.

20. The vehicle of claim 19 further comprising:
a center console,
wherein, the housing is disposed at the center console.

\* \* \* \* \*

UNITED STATES PATENT AND TRADEMARK OFFICE
CERTIFICATE OF CORRECTION

PATENT NO. : 11,878,619 B2
APPLICATION NO. : 17/108611
DATED : January 23, 2024
INVENTOR(S) : Acre et al.

Page 1 of 1

It is certified that error appears in the above-identified patent and that said Letters Patent is hereby corrected as shown below:

In the Claims

Column 11:
Claim 1, Line 15;
"form" should be --forms--.
Claim 1, Line 18;
After "body" insert --of--.

Signed and Sealed this
Twelfth Day of March, 2024

*Katherine Kelly Vidal*

Katherine Kelly Vidal
*Director of the United States Patent and Trademark Office*